(12) United States Patent
Scott et al.

(10) Patent No.: US 10,588,592 B2
(45) Date of Patent: Mar. 17, 2020

(54) SCATTER IN X-RAY APPARATUS AND METHODS OF THEIR USE

(71) Applicant: IBEX Innovations Ltd., Sedgefield, Durham (GB)

(72) Inventors: Paul Scott, Sedgefield (GB); Gary Gibson, Sedgefield (GB); Neil Loxley, Sedgefield (GB)

(73) Assignee: IBEX Innovations Ltd., Sedgefield Durham (GB)

( * ) Notice: Subject to any disclaimer, the term of this patent is extended or adjusted under 35 U.S.C. 154(b) by 110 days.

(21) Appl. No.: 15/516,749

(22) PCT Filed: Oct. 5, 2015

(86) PCT No.: PCT/GB2015/052908
§ 371 (c)(1),
(2) Date: Apr. 4, 2017

(87) PCT Pub. No.: WO2016/051212
PCT Pub. Date: Apr. 7, 2016

(65) Prior Publication Data
US 2017/0238894 A1    Aug. 24, 2017

(30) Foreign Application Priority Data

Oct. 4, 2014 (GB) .................................... 1417637.4
Dec. 19, 2014 (GB) .................................... 1422752.4

(51) Int. Cl.
*A61B 6/00* (2006.01)
*G01T 1/29* (2006.01)
(Continued)

(52) U.S. Cl.
CPC .......... *A61B 6/5282* (2013.01); *A61B 6/4291* (2013.01); *G01T 1/2985* (2013.01);
(Continued)

(58) Field of Classification Search
CPC ....... A61B 6/00; A61B 6/5282; A61B 6/4291; A61B 6/5258; A61B 6/483; A61B 6/4233;
(Continued)

(56) References Cited

U.S. PATENT DOCUMENTS 1,164,987 A    12/1915  Bucky
4,413,353 A    11/1983  Macovski et al.
(Continued)

FOREIGN PATENT DOCUMENTS

EP    0223305 A1    5/1987
GB    2498615 B    6/2016
(Continued)

OTHER PUBLICATIONS

Written Opinion of the International Searching Authority, Application No. PCT/GB2015/052908, filed Oct. 5, 2015.
(Continued)

*Primary Examiner* — Jurie Yun
(74) *Attorney, Agent, or Firm* — MacMillan, Sobanski & Todd, LLC

(57) ABSTRACT

An x-ray apparatus comprises an x-ray source and an x-ray detector and there between a member that is configured to perturb x-ray photons incident thereon. The apparatus further comprises a first database of values representative of material type and material thicknesses, a second database of scatter radiation values indicative of material type and/or material thicknesses, a processor configured to perform an algorithm which compares the output signal of the x-ray detector with values in the first database and to output a most likely material and/or thickness from the first database; selects from the second database the scatter radiation asso-
(Continued)

ciated with the material type and/or material thickness; and removes the scatter radiation from an output signal of the x-ray detector.

15 Claims, 13 Drawing Sheets

(51) Int. Cl.
  *G06F 19/00* (2018.01)
  *G06T 5/00* (2006.01)
  *G06T 7/00* (2017.01)

(52) U.S. Cl.
  CPC ............ *G06F 19/321* (2013.01); *G06T 5/002* (2013.01); *G06T 7/0012* (2013.01); *G06T 2207/10116* (2013.01); *G06T 2207/20182* (2013.01)

(58) Field of Classification Search
  CPC .. G06T 5/00; G06T 5/002; G06T 7/00; G06T 7/0012; G06T 2207/10116; G06T 2207/20182; G06F 19/00; G06F 19/321
  USPC ........ 378/62, 98.4, 98.8, 147, 149, 154, 155
  See application file for complete search history.

(56) References Cited

U.S. PATENT DOCUMENTS

| | | | |
|---|---|---|---|
| 7,551,716 | B2 | 6/2009 | Rührnschopf |
| 8,976,928 | B2 | 3/2015 | Takahashi |
| 9,519,068 | B2 | 12/2016 | Gibson |
| 2005/0111626 | A1 | 5/2005 | Xu et al. |
| 2005/0190888 | A1 | 9/2005 | Schmitt |
| 2006/0008046 | A1 | 1/2006 | Rührnschopf |
| 2009/0086907 | A1 | 4/2009 | Smith |
| 2009/0290682 | A1 | 11/2009 | Star-Lack et al. |
| 2011/0311032 | A1 | 12/2011 | Miller |
| 2012/0148156 | A1 | 6/2012 | Sehnert |
| 2013/0044860 | A1 | 2/2013 | Nicholson et al. |

FOREIGN PATENT DOCUMENTS

| | | |
|---|---|---|
| JP | H01255459 A | 10/1989 |
| JP | H05303154 A | 11/1993 |
| JP | H0614911 A | 1/1994 |
| JP | H10314152 A | 12/1998 |
| JP | 2008502395 A | 1/2008 |
| JP | 2009018110 A | 1/2009 |
| SU | 962797 A1 | 9/1982 |
| WO | 9730459 A1 | 8/1997 |
| WO | 2011058612 A1 | 5/2011 |
| WO | 2011027390 A1 | 1/2013 |

OTHER PUBLICATIONS

GB Search Report, Application No. GB1422752.4, dated Nov. 9, 2015.
GB Search Report, Application No. GB1517571.4, dated May 31, 2016.
Sun, et al., Correction for patient table-induced scattered radiation in cone-beam computed tomography (CBCT), Med. Phys., 38, (4), Apr. 2011, pp. 2058-2073.
Rührnschopf, et al., A general framework and review of scatter correction methods in cone beam CT. Part 2: Scatter estimation approaches, Med. Phys., 38 (9), Sep. 2011, pp. 5186-5199.
Ahn, et al., "A Scatter Correction Using Thickness Iteration in Dual-Energy Radiography", IEEE Transactions on Nuclear Science, vol. 53, No. 1, Feb. 2006, pp. 133-138.
Japanese Office Action, Application No. 008085, dated Jan. 15, 2019.
EP Communication, Appliction No. 157942194, dated Feb. 7, 2019.
PCT Written Opinion, Application No. PCT/GB2015/052908, dated Feb. 10, 2016.

SCATTER IN X-RAY APPARATUS AND METHODS OF THEIR USE

FIELD OF THE INVENTION

The present invention relates to x-ray equipment that typically utilises anti-scatter grids, and in particular to an apparatus that provides for scattered x-rays to be utilised in analysis of an x-ray image.

BACKGROUND OF THE INVENTION

When an object is subjected to x-ray radiation some of the x-ray photons are absorbed and some pass through the object, unscattered, to impinge on an x-ray detector. This is referred to as "direct radiation". Some x-rays are absorbed and others are scattered. The intensity of the scatter produced may exceed the magnitude of the direct radiation detected by the detector. The scattered radiation results in poor image quality by reducing contrast and increasing noise. Absorbed x-rays provide the contrast in an x-ray image. If scattered x-ray photons hit the detector random noise in the image is increased since it is not possible to identify where the scattered x-ray photons have come from.

The most widely adopted technique used to address the problem of scatter is to place an anti-scatter grid between the x-ray detector and the object under test. An anti-scatter grid comprises a series of spaced apart parallel lamellae formed of x-ray absorbing material. A large proportion of scattered x-rays engage one of the lamella and are absorbed. It is therefore predominantly the direct radiation that is detected by the x-ray detector when an anti-scatter grid is present.

The original anti-scatter grid is described in U.S. Pat. No. 1,164,987 (Bucky).

One of the problems with anti-scatter grids is that in addition to reducing the effect of scatter in the detected image, the x-ray absorbing lamellae absorb some of the direct radiation, that is those photons travelling in the path of the lamellae.

In order compensate for the photons lost in the anti scatter grid and hence the reduced image quality, it is common practice to increase the x-ray flux. However, this is disadvantageous where the x-ray imaging is of x-ray sensitive material. This is of most concern in medical imaging where the x-ray radiation dose to the patient must be increased to compensate for the presence of the anti-scatter grid.

Some attempts have been made to reduce the x-ray power used in x-ray imaging.

U.S. Pat. No. 7,551,716 instead of using an anti-scatter grid uses mathematical methods to determine approximately the scatter x-ray photons. It is asserted that by utilising mathematical methods to determine approximately the scatter x-ray photons, the x-ray dose can be reduced or the signal to noise ratio increased when compared with an x-ray apparatus using an anti-scatter grid.

An x-ray apparatus that includes a multi-absorption plate is described in the applicant's patent application published under number GB2498615. In this x-ray apparatus the x-ray energy spectrum is perturbed in many different ways. This apparatus and method provides information that allows material properties to be identified. Patent application number GB2498615 is incorporated herein by reference.

The prior art addresses problems caused by scatter radiation either by using an anti-scatter grid to reduce substantially the scatter radiation, or by applying a mathematical correction to remove an estimation of what the scatter radiation might be from an x-ray image.

The present invention addresses the issue of scatter in a new way which involves measuring both the direct and the scattered radiation. This is achieved by imposing a change on the apparatus that affects both the direct and scattered radiation.

Scatter radiation has previously been considered as impacting negatively on an x-ray image. Previous attempts at combatting the problem of scatter focus on optimising the removal of scatter radiation, so that the image is as far as possible formed by direct x-ray radiation impinging on the x-ray detector.

As well as providing for measurement of scatter radiation, the present invention provides for scattered radiation to be used in the identification of materials and thicknesses of materials and in improving the contrast to noise ratio.

By comparing a measured output signal from an x-ray detector to an independent measure of the scattered radiation it is then possible to identify the scatter radiation within the image that contains direct radiation and scatter radiation, and to remove the scatter radiation from the image. It is thereby possible to increase the contrast to noise ratio. In the context of medical applications and other applications where x-rays are used to analyse materials that may be harmed by x-rays, the present invention allows either the dose to be reduced to produce a similar standard of image, or using the same x-ray dose a better image can be generated.

SUMMARY OF THE INVENTION

According to a first aspect of the invention there is provided an x-ray apparatus comprising an x-ray source and a multi-pixel x-ray detector and therebetween a member that is configured to perturb x-ray photons incident thereon, wherein the member is adapted so as to perturb x-ray photons incident thereon differently dependent upon the angle of incidence of such x-ray photons, the member including a plurality of elements formed of a material that exhibits at least partial translucence to x-ray photons, the apparatus further comprising
a first database of values representative of material type and/or material thicknesses,
a second database of scatter radiation values indicative of material type and/or material thicknesses,
a processor configured to perform an algorithm which:
  i) compares the output signal of each pixel of the x-ray detector with values in the first database and to output a most likely material and/or thickness from the first database;
  ii) selects from the second database the scatter radiation associated with the material type and/or material thickness in step (i);
  iii) removes the scatter radiation from the output signal of the x-ray detector.

Advantageously, the algorithm includes the step of modifying the output signal of the x-ray detector by adding the removed scatter radiation to the output signal at a spatial location of the detector that the x-ray photons of the removed scatter radiation would have interacted with had they not been scattered.

The first database of values representative of material type and/or thickness may be created substantially in the absence of scatter, for example by utilising an anti scatter grid.

The algorithm may be performed for the x-ray output signal for each pixel.

Preferably, the algorithm includes the step of performing a materials and/or thickness identification step on the output of step iii, utilising the identified materials/and or thickness in at least one further iteration of steps ii and iii of the algorithm.

Advantageously, the algorithm includes the further step of determining whether the modified x-ray output signal is optimised.

The step of determining whether the modified x-ray output signal is optimised may comprise comparing a value indicative of material type and thickness in the image of the current iteration with the value indicative of material type and/or thickness in the image of the previous iteration, or an average of the values indicative of material type and/or thickness in a number of previous iterations, and determining whether the values indicative of material type and/or thickness in the image of the current iteration is within a threshold limit the value indicative of material type and/or thickness of the previous iteration, or the average of the values indicative of material type and/or thickness in a number of previous iterations. If the compared values are within the threshold then the re-iteration of steps (i) to (iii) of the algorithm may be halted.

The algorithm may comprise the further step of modifying the output signal of the x-ray detector by adding the removed scatter radiation to the output signal at a spatial location of the detector that the x-ray photons of the removed scatter radiation would have interacted with had they not been scattered.

Preferably, the scatter values in the second database of scatter radiation values indicative of material type and/or thickness are scatter kernels.

A scatter kernel may be defined as is a representation of the scatter from a single track of x-ray photons through a material.

The database may be populated with scatter kernels representing the identity and/or thickness of some of a range of materials of interest.

The step of removing scatter radiation from the output signal of the x-ray detector may include, for each pixel of the detector, the step of interpolating a scatter kernel from scatter kernels selected from the database in step ii, and may also include the further step of generating a scatter estimate for the whole x-ray detector output signal from the interpolated scatter kernels associated with each pixel.

Advantageously, the member is a multi-absorption plate (MAP), that being a plate comprising a plurality of different regions, different region having a different transparency to incident x-ray energy. The plurality of different regions may be formed in a repeating pattern, with adjacent regions having a different transparency to incident x-ray energy.

It is preferred that the member is held in a static position during image capture.

According to a second aspect of the invention there is provided an x-ray apparatus comprising an x-ray source and a multi-pixel x-ray detector and therebetween a member that is configured to perturb x-ray photons incident thereon, wherein the member is adapted so as to provide at least two different configurations of the apparatus and wherein the member perturbs the x-ray photons differently in the different configurations.

Preferably, the member is moveable so as to provide the at least two different configurations of the apparatus.

In one embodiment the member is a multi-absorption plate (MAP), that being a plate comprising a plurality of different regions, each region having a different transparency to incident x-ray energy. Such a MAP may be movable in one axis, in two axes or three axes and the axes may be orthogonal to one another.

By moving the member, the part of the member that any one x-ray photon is likely to encounter will differ in each different configuration and hence the scatter pattern for each different configuration of the apparatus will differ.

In the case of direct radiation, the effect of moving between known different configurations, will always be the same. That is moving the member from a configuration (a) to a configuration (b) will always have the same effect on the direct radiation. Moving the member from configuration (b) to configuration (c) will always have the same effect on the direct radiation, although that effect may be different to the effect of moving from configuration (a) to configuration (b). With this knowledge it is possible to identify the direct radiation and hence the scatter radiation, because the scatter radiation is that which is not direct radiation.

In another embodiment the member closely resembles an anti-scatter grid, except that the individual lamellae are mounted rotatably within a frame. Rotating the lamellae within the frame changes the configuration of the apparatus, since the scatter pattern where the lamellae are parallel with the axis extending from the x-ray source to the x-ray detector will differ from the scatter pattern where the lamellae lie at say 5 degrees from parallel with said axis.

In another embodiment, instead of moving a MAP or configuring the lamellae of an anti-scatter grid so as to rotate, the member may be formed of a memory metal that changes between a flat configuration and a flexed configuration when a signal, such as an electric current, is applied. In another embodiment, the member is formed of a piezoelectric material, which changes size on application of an electric current thereto.

The member may comprise individual lamellae rotatably mounted within a frame.

The member may be formed of a memory metal that changes between configurations by changing shape upon application of a signal thereto. The member may be formed of a memory metal that changes between flat and flexed configurations upon receipt of the signal.

The member may be formed of a piezoelectric material, which changes size and/or shape on application of an electric current thereto According to another aspect of the invention there is provided an x-ray apparatus comprising an x-ray source and a multi-pixel x-ray detector and therebetween a member that is configured to perturb x-ray photons incident thereon, wherein the member is adapted so as to perturb x-ray photons incident thereon differently dependent upon the angle of incidence of such x-ray photons, the member including a plurality of elements formed of a material that exhibits at least partial translucence to x-ray photons.

Preferably, the elements extend further in the direction of the axis that extends from the x-ray source to the x-ray detector than in a direction perpendicular thereto.

When a scattered x-ray photon impinges upon one of the elements, whether the scattered x-ray photon passes through the element or is absorbed by it, and if it passes through the element its energy, will depend on the angle of incidence of the x-ray photon on the element. This is because the angle of incidence of the x-ray photon determines the thickness of material that the incident x-ray photon must pass through (of course an x-ray photon incident on an element proximate a corner thereof may experience less thick material than it would have done had it been incident on the element distal from a corner for the same angle of incidence).

According to another aspect of the invention there is provided a method of removing scatter radiation from an x-ray image comprising the steps of: subjecting a material under test to x-ray photons in an apparatus of the first aspect of the invention and changing the configuration of the member during the test; analysing the x-ray image and identifying direct radiation and scatter radiation in the x-ray image and removing the identified scatter radiation from the x-ray image.

The method of removing scatter radiation from an x-ray image may comprise the further step of identifying material type and/or material thickness.

The material type and/or thickness may be identified from the removed scatter radiation. The x-ray image may be modified in accordance with identified material types and/or thicknesses.

According to another aspect of the invention there is provided a method for identifying material and/or material thickness from scatter radiation in the raw x-ray image which includes both scattered and direct x-ray radiation.

When an unknown material and/or thickness is tested using the apparatus of the invention, the resulting scatter patterns are compared with scatter patterns in the database the most likely material and/or thickness can be identified, thereby allowing the material and/or thickness to be identified.

To carryout materials and/or thickness identification known materials of known thickness may be subject to x-ray photons in an apparatus of the second aspect of the invention with the configuration of the member being changed during the test. This allows different scatter patterns coinciding with the different configurations of the member to be generated for a known material and/or thickness. This can be stored in a database. This may be done on a per pixel basis, that is for the output of each pixel of the multi-pixel detector.

Scatter patterns for known material types and/or thickness may also be recorded and stored in a database.

BRIEF DESCRIPTION OF THE DRAWINGS

In the Drawings, which illustrate preferred embodiments of the invention, and are by way of example:

FIG. 12a shows a histogram of counts v intensity for the image shown in FIG. 11a;

DETAILED DESCRIPTION OF THE DRAWINGS

Figure 1:
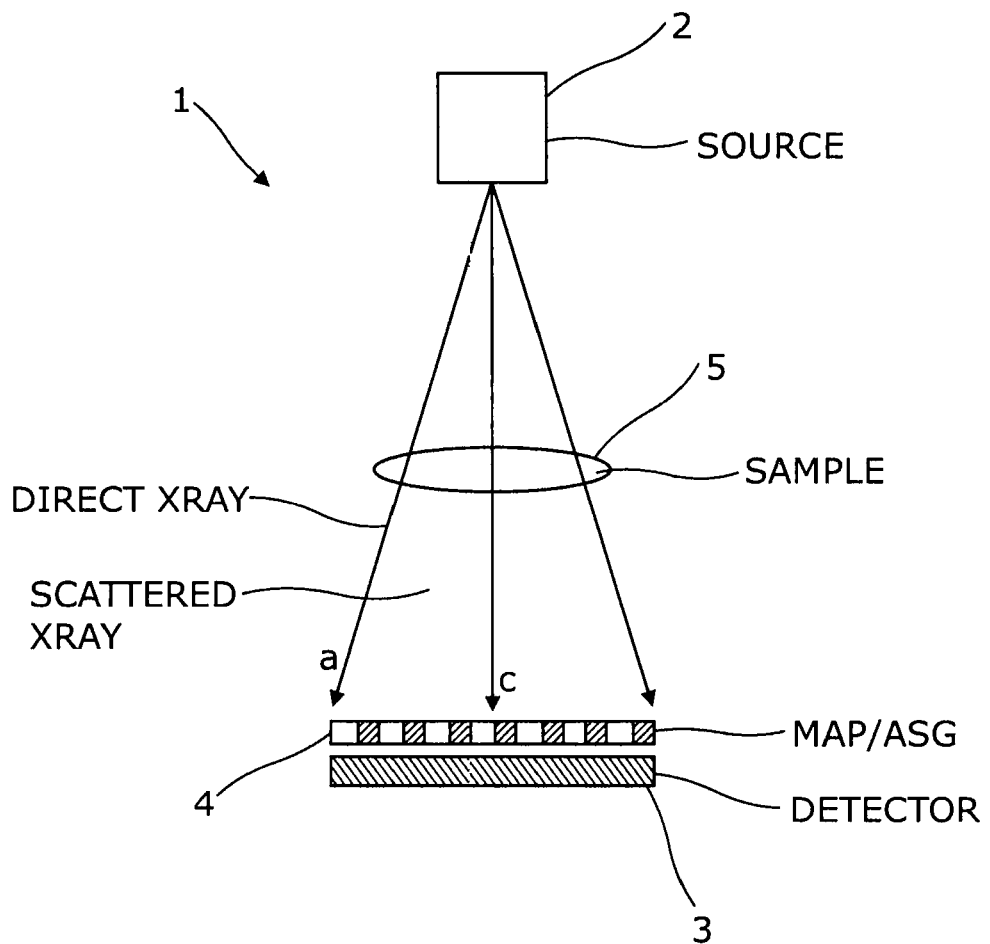
FIG. 1 is a schematic representation of an apparatus according to the invention.

FIG. 1 shows a general arrangement of an apparatus 1 according to the invention. An x-ray source 2 is aligned with a detector 3, with a member 4, in this case a multi-absorption plate or anti-scatter grid, is situated adjacent the detector 3 on the source side thereof. The sample under test 5 is situated between the source 2 and the multi-absorption plate (MAP) or anti-scatter grid 4.

FIGS. 2 to 7 show a number of different alternative arrangements of the member.

Figure 2:
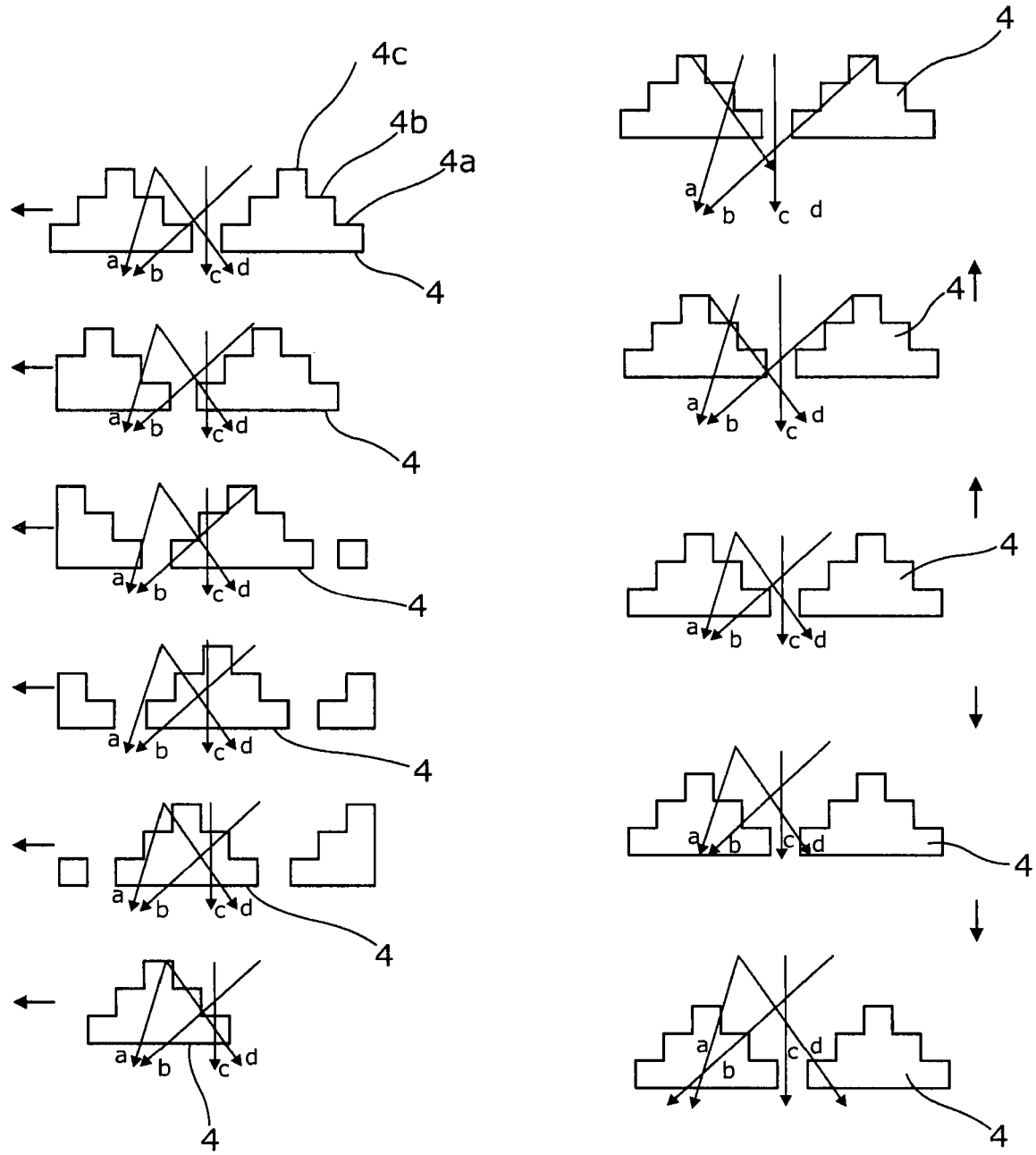
FIG. 2 illustrates examples of a member of the invention.

In FIG. 2, the member 4 is a MAP which comprises a series of symmetrical steps 4a, 4b, 4c, so that the central part 4c of the MAP presents three times the thickness of material when compared with the outermost parts of the MAP. The MAP may be moved sideways as shown on the left in FIG. 2, or upwards and downwards, as shown on the right in FIG. 2. Looking now at the representations on the left, these show six different configurations of the apparatus. Each representation beneath the top most shows the new position of the MAP 4 in solid shading and the position of the MAP in the top most representation in shadow. Of course in addition to or as an alternative, rather than the MAP 4 moving sideways, it may move back and forth.

Looking at the representations on the right, these show five different configurations of the MAP. The central representation shows the MAP prior to movement thereof. The representations above the central representation show two steps of movement upwards in the vertical direction, whereas the representations below the central representation show two steps of movement downwards in the vertical direction.

As will be appreciated from the FIG. 2 drawings, as the MAP is moved either horizontally or vertically, the thickness of material that an x-ray photon travelling on a certain path must pass through will change as the position of the MAP changes.

Figure 3:
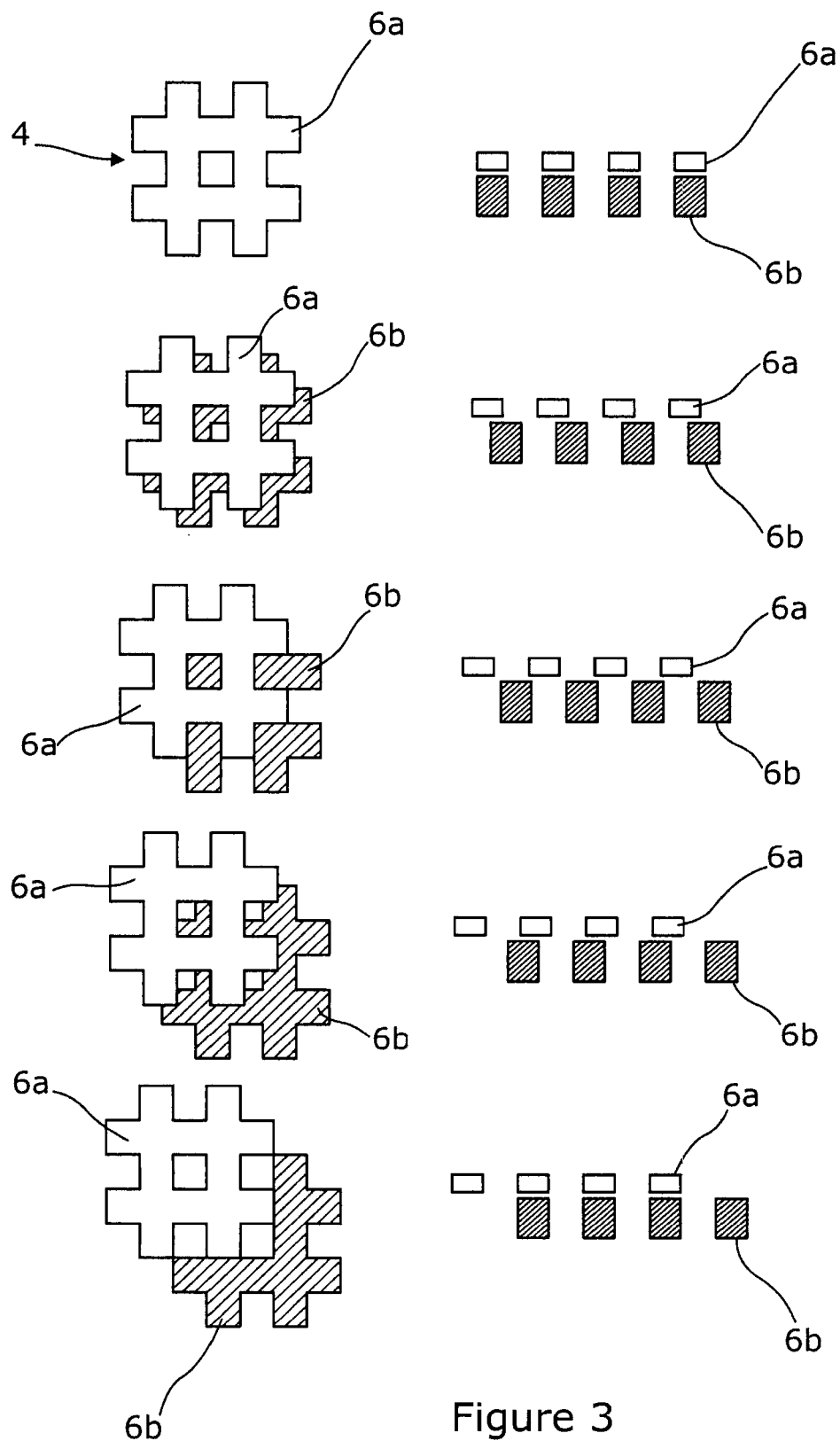
FIG. 3 illustrates examples of an alternative member of the invention.

In FIG. 3 the member 4 is made up of multiple plates 6a, 6b which overlie one another. Each plate 6a, 6b is made up of a grid of material. In this embodiment, the upper plate 6a is thinner than the lower plate 6b. In the top most representation, the grids 6a, 6b are aligned. In the representation immediately below the top most representation, the upper grid 6a has been moved to the left so that the material of the upper grid 6a partially overlies the spaces of the lower grid. As the upper grid is moved further, the upper grid 6a moves so that it overlies the spaces of the lower grid 6b and with further movement, as shown in the two lowermost representations, the upper grid 6a moves such that three sections of material of the upper grid 6a become aligned with material of the lower grid, with the rightmost section of the lower grid not covered by the upper grid. Of course, what is important in this embodiment is relative movement between the plates 6a, 6b. Such movement may be of the upper and/or lower plates 6a, 6b.

Again, the skilled person will appreciate that x-ray photons scattered by the material under test will be affected differently according to how the upper and lower grids are position relative to one another.

Figure 4:
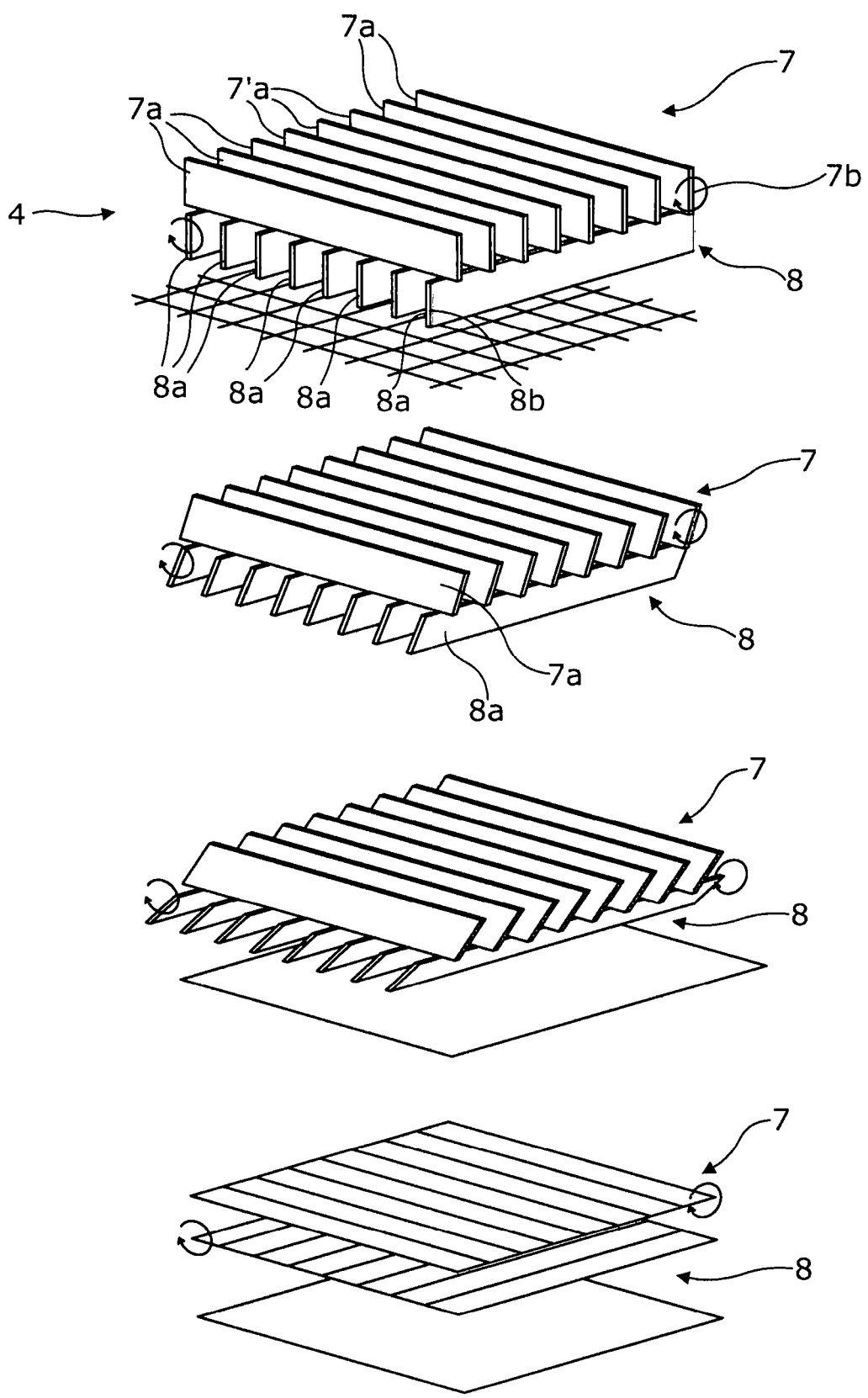
FIG. 4 illustrates examples of a further alternative member of the invention.

In FIG. 4 the member 4 comprises upper and lower sets 7, 8 of lamella 7a, 8a that are configured for mounting in a frame (not shown) such that relative rotation with respect to such a frame is possible. As the lamellae 7a, 8a rotate the thickness of material that an x-ray photon (be that a scattered x-ray photon or a direct x-ray photon) travelling on a certain path must pass through will change. As can be seen from the four representations in FIG. 4, the lamellae 7a, 8a can move from a position where the lamellae 7a, 8a lie in substantially the same plane as the axis extending from the x-ray source to the detector to a position where the lamellae 7a, 8a lie perpendicular to that axis.

The material from which the lamellae 7a, 8a are formed may be opaque to x-ray photons or may be translucent thereto. The effect of translucence of the lamella is explained in greater detail below with reference to FIG. 5.

Figure 5:
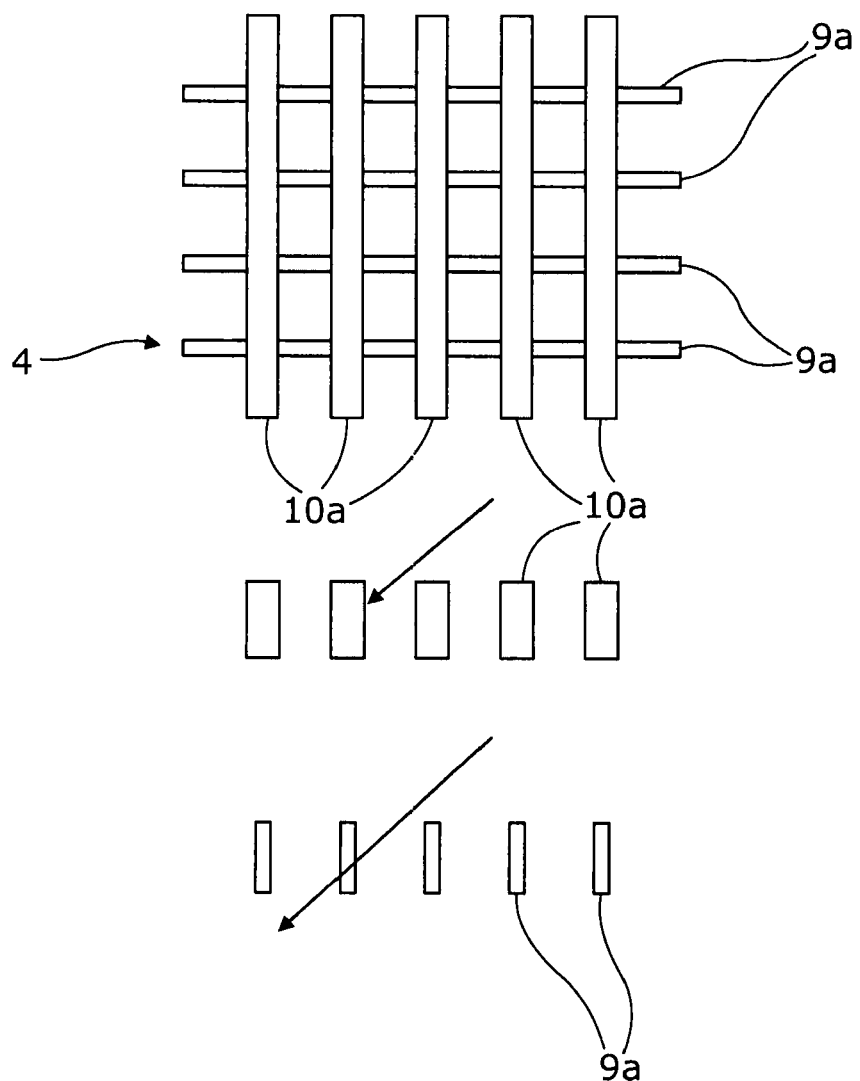
FIG. 5 illustrates examples of a further alternative member of the invention.

FIG. 5 shows a member 4 in the form of an anti-scatter grid having lamellae 9a, 10a extending in two orthogonal directions. The lamellae 9a extending left to right are translucent to x-ray photons, whereas the lamellae 10a extending perpendicular thereto are opaque to x-ray photons. Scattered x-ray photons impinging upon the translucent lamella at a very small angle to the axis extending from the source to the x-ray detector would have to pass through a much greater thickness of material than would a scattered x-ray photon impinging upon the translucent lamella at a significantly greater angle, for example tending towards perpendicular to the aforementioned axis. Such an x-ray photon may pass through the lamella with little attenuation. Hence, it will be understood that scatter x-ray photons are attenuated according to the angle of incidence on the translucent lamella.

The member 4 illustrated in FIG. 5 may be used either in a static or dynamic arrangement.

In a dynamic arrangement the member 4 is mounted so that it may be moved, which movement may be in a similar manner to that described with reference to FIGS. 2 and 3. As described with reference to those Figures, the effect on direct x-ray photons of moving the member 4 described with reference to FIG. 5 in a certain manner is always the same, and this expected change can be used to identify direct x-ray photons and hence scattered x-ray photons.

In the static arrangement the member does not have different configurations so its effect on direct x-ray photons is not variable. It is possible, however to identify scattered x-ray photons.

It is known that for different material types and thicknesses the pattern of scattered x-ray photons is characteristic of the material and thickness. By testing different known materials of different known thicknesses, a database of x-ray detector outputs can be built up. Such x-ray detector outputs include the signal recorded at each pixel. When a sample of unknown material is tested in the apparatus 1, identification of material type and/or thickness of the sample 5 may be achieved by comparing data in the form of signals received at adjacent pixels, or differences between the signals received at adjacent pixels, with a database of signals or differences between signals associated with different known material types and/or thicknesses and making a determination as to the material type and/or thickness of the sample based on the information from the database that corresponds most closely to the detected signals or differences between signals.

Figure 6:
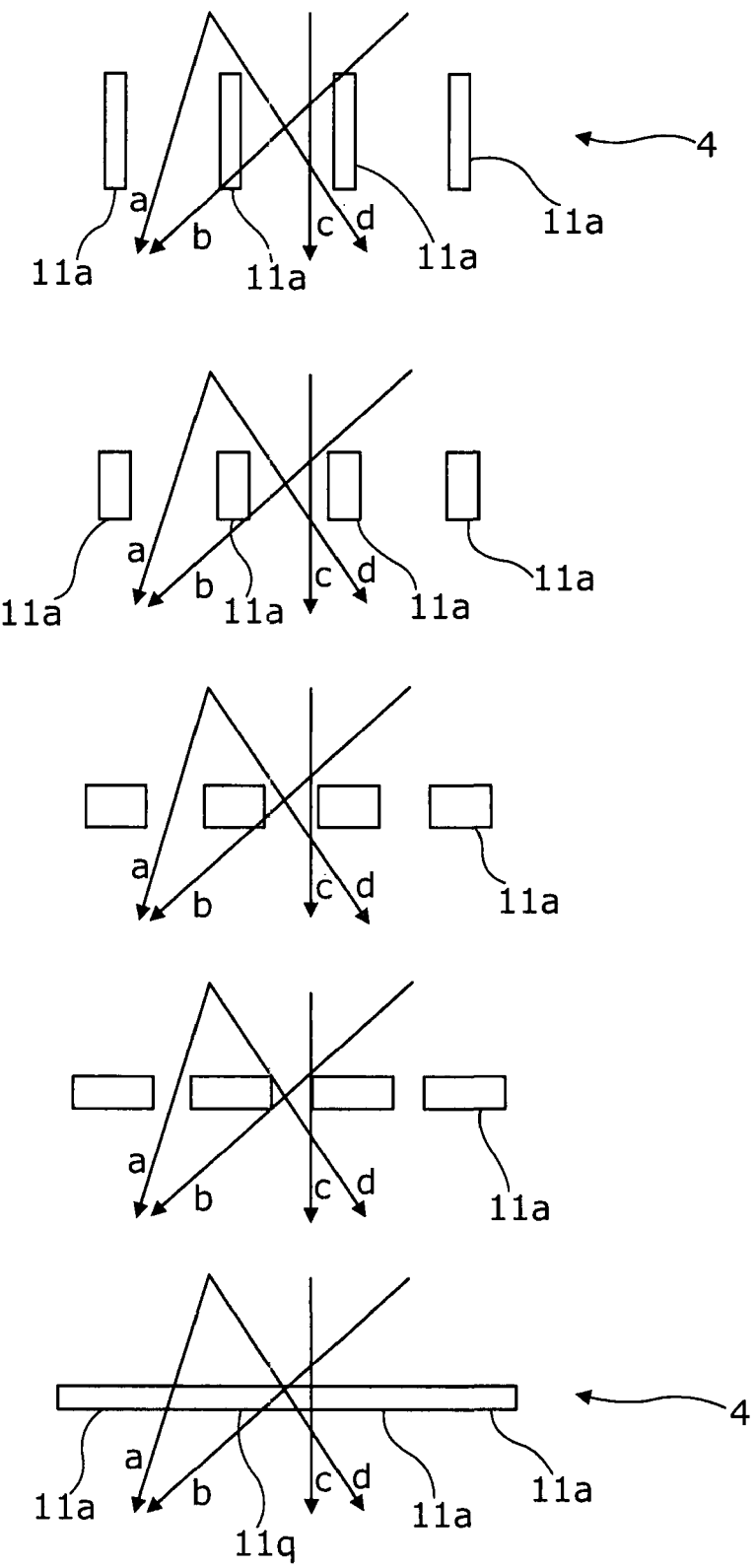
FIG. 6 illustrates examples of a further alternative member of the invention.
Figure 7:
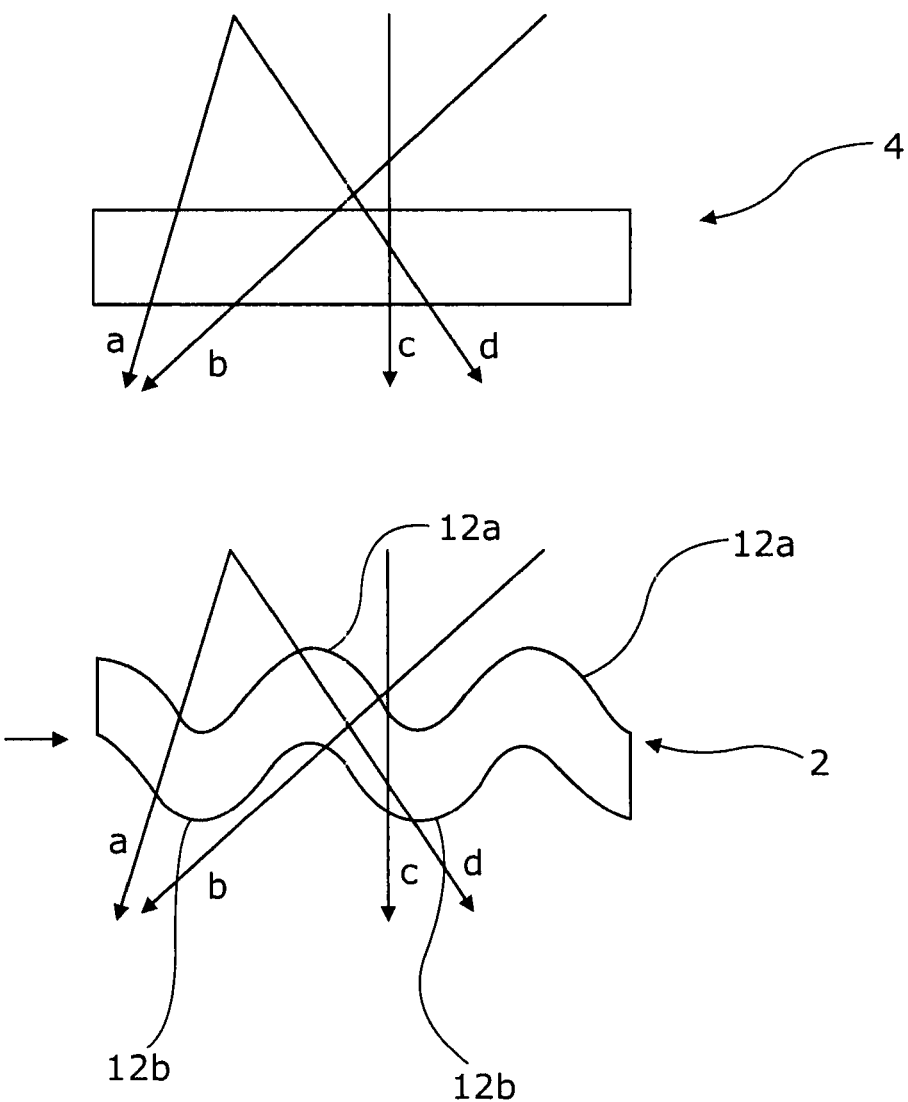
FIG. 7 illustrates examples of a further alternative member of the invention.

FIGS. 6 and 7 are similar in that the configuration of the member 1 is changed by affecting physical changes to the material from which the member is formed. FIG. 6 illustrates a member 1 formed of four lamellae 11a each of a piezo electric material that changes shape according to the charge applied to it. In one configuration (the uppermost representation) the lamellae 11a are deep and narrow, with the spaces between parallel lamellae being significantly greater than the width of the individual lamella 11a. Charge is applied and the piezo electric material changes shape, the individual lamella becoming shallower an wider. As the applied charge is changed still further the material changes shape until the lamellae 11a together present a continuous flat surface as shown in the lowermost representation of FIG. 6.

In the embodiment of FIG. 7 the member 1 is formed of a memory metal, which moves between a planar configuration shown in the uppermost representation and a corrugated configuration which provides curved regions 12a, 12b. The member 1 changes shape between the two configurations shown depending on the electrical current applied thereto.

In FIGS. 2, 3, 6 and 7 the same arrows a, b, c and d are shown. These represent the path of an x-ray photon and the material of the member 1 that said photon encounters depending on the configuration of the member. One skilled in the art will readily appreciate that by changing the configuration of the member the effect thereof on x-ray photons can be significant.

Figure 8A:
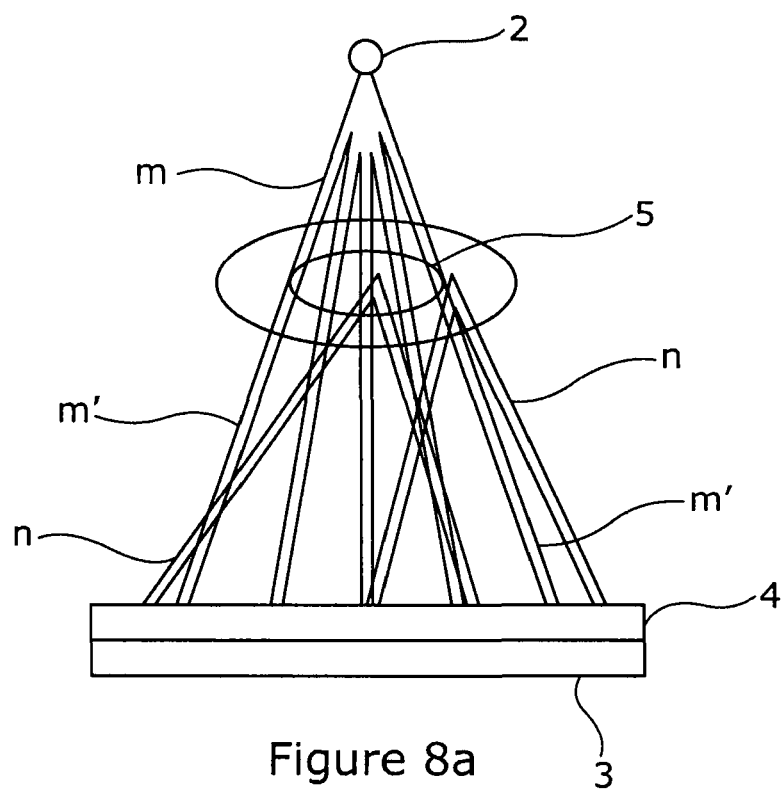
FIGS. 8a and 8b illustrates an alternative embodiment of the invention.
Figure 8B:
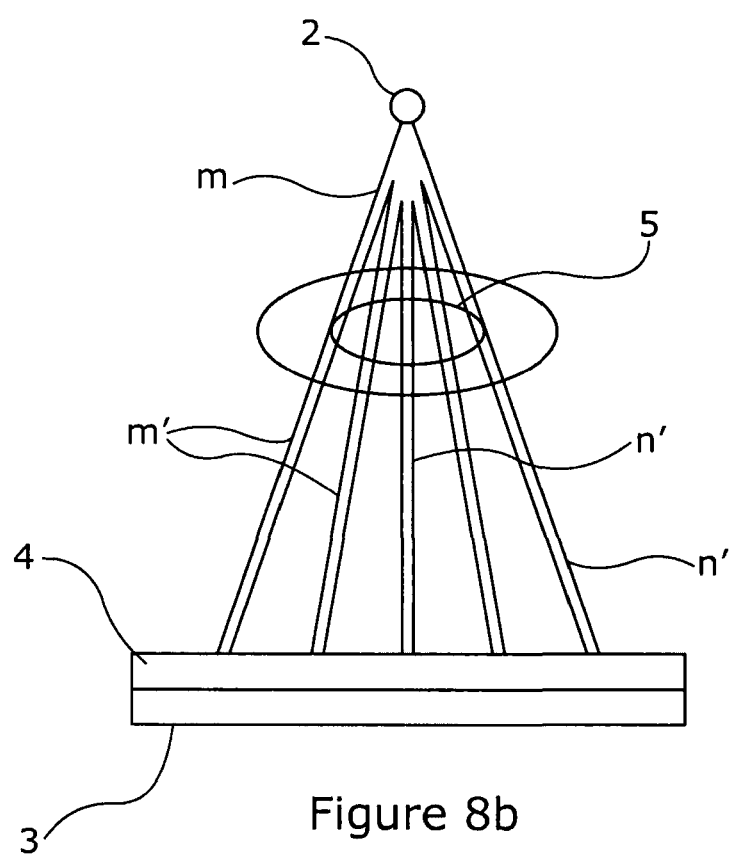

FIG. 8a, show an apparatus 1 according to another embodiment of the invention. An x-ray source 2 is aligned with a detector 3, with a multi-absorption plate (MAP) 4 situated adjacent the detector 3 on the source side thereof. The MAP 4 may be of the type described with reference to FIG. 2 or a MAP 16 as described with reference to 13. The key difference between the embodiment of the invention illustrated in FIG. 2 and the embodiment illustrated in FIGS. 8a and 8b is that of movement of the MAP 4. In the FIG. 2 embodiment the MAP 4 moves with respect to the source 2 and detector 3, whereas in the embodiment of FIGS. 8a and 8b the MAP 4 is stationary.

Figure 13:
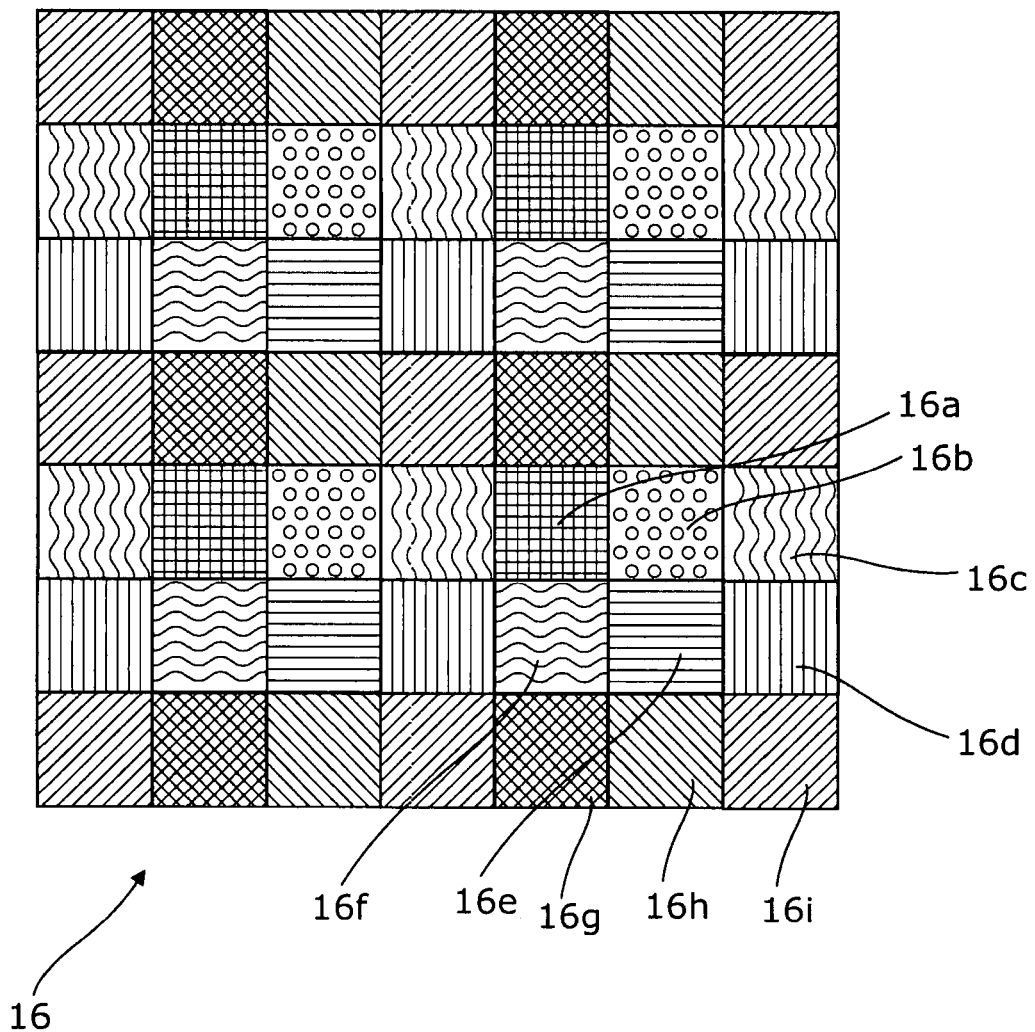
FIG. 13 is a view of a multi-absorption plate shown from above with the plate oriented as in FIGS. 8a and 8b.

The MAP 16 illustrated in FIG. 13 comprises different regions 16a-16i. The different regions of the plate have different x-ray absorption capabilities. They may have different thicknesses, or be formed of different materials for example.

FIG. 8a illustrates what happens to x-ray photons that are incident on a material under test 5. As explained above, of the x-ray photons m emitted from the x-ray source 2, some of the x-ray photons m' pass straight through the material under test 5 to impinge on the detector 3, these x-ray photons representing "direct radiation", some are absorbed and some x-ray photons n are scattered.

The scatter x-ray photons n are undesirable. This embodiment of the invention allows the scattered x-ray photons n shown in FIG. 8a to be removed from the image and re-assigned as pseudo-direct radiation n' to the direct radiation m' with which they were associated. The result is that in FIG. 8b the output of any one pixel of the detector 3 resulting x-ray photons impinging thereon comprises the direct radiation m' and the re-assigned pseudo-direct radiation n'. This increases the contrast and hence the contrast to noise ratio in the image generated by the detector 3, and also provides a more desirable image because the scattered x-ray photons n are not removed as would be the case with an anti-scatter grid, but are added to the output signal at a spatial location of the detector that the x-ray photons would have interacted with had they not been scattered. The result is therefore to boost the image contrast.

In order to remove the scatter photons n from the detected image and re-assign them as pseudo-direct radiation n' the signals detected by the detector 3 are processed as follows:

A database of the scatter patterns of different materials and different thicknesses thereof is created. This is done using a simulation model illustrated in FIG. 10, which simulates how different materials and different thickness thereof scatter when a pencil beam of x-ray photons are incident thereon. Instead of using a simulation model, the data for the database could be gathered using real apparatus and samples, the samples being of different material type and/or thickness.

By using a pencil beam that is aligned with one pixel of a multi-pixel detector, one can be certain that the x-ray photons reaching the pixel with which the source is aligned represent for the most part "direct radiation" or scattered radiation that has been scattered through a very small angle from the path of the direct radiation and that all x-ray photons detected by other pixels are scattered x-ray photons which came from the incident pencil beam. It is therefore possible to establish the signature scatter pattern of any material of a given thickness. By repeating this process for different thicknesses of the same materials, the signature patterns for different thicknesses of the same material can be established. Similarly, repeating the process for different materials and/or different thicknesses of those materials, a database of signature scatter patterns can be built up.

A Monte Carlo model of the x-ray system and x-ray physics was created using a software package called GEANT4 which simulates the passage of particles through matter. The model was used to simulate the result of a pencil beam of x-ray photons being incident upon different materials and thicknesses thereof. The results for different materials and different thickness thereof are recorded.

Figure 10:
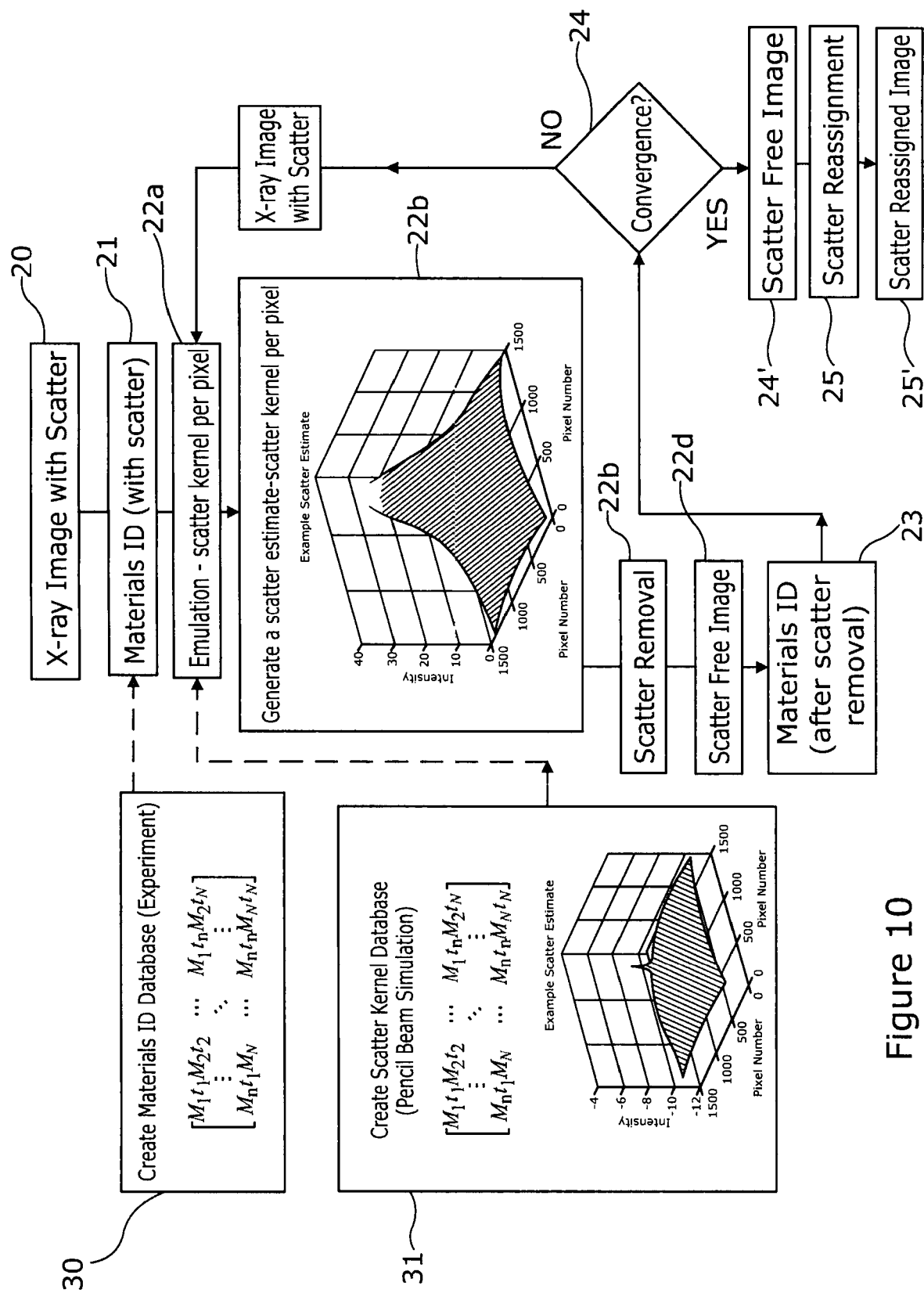
FIG. 10 is another flow chart illustrating the method of operation of the embodiment of the invention illustrated in FIGS. 8a and 8b.

Each scatter pattern has a shape similar to that shown in FIG. 10 in Graph 1. In relation to scatter, this is also known as a scatter kernel. For any one scatter kernel, the scattered photons represented by all the x-ray photons incident on pixels of the detector 2 that are not aligned with the pencil beam can be identified, and removed from the image. To improve the image further the removed scatter radiation may be added back to the photon intensity recorded at the pixel or pixels aligned directly with the pencil beam as direct radiation. Hence, the resulting output intensity at the pixel or pixels is the sum of direct radiation output signal and the output signal at a spatial location of the detector that the x-ray photons of the removed scatter radiation would have interacted with had they not been scattered.

However, creating and using a database of signature scatter kernels for all materials of interest and their thickness would require vast data storage capacity and very powerful processing capability, or alternatively, using the data stored in such a database would be very slow.

The model of this embodiment of the invention therefore uses an interpolation technique in order to derive scatter kernels for combinations of materials and their thicknesses which have not themselves been specifically simulated. The technique of interpolation and in this embodiment emulation is not in itself new.

Figure 9:
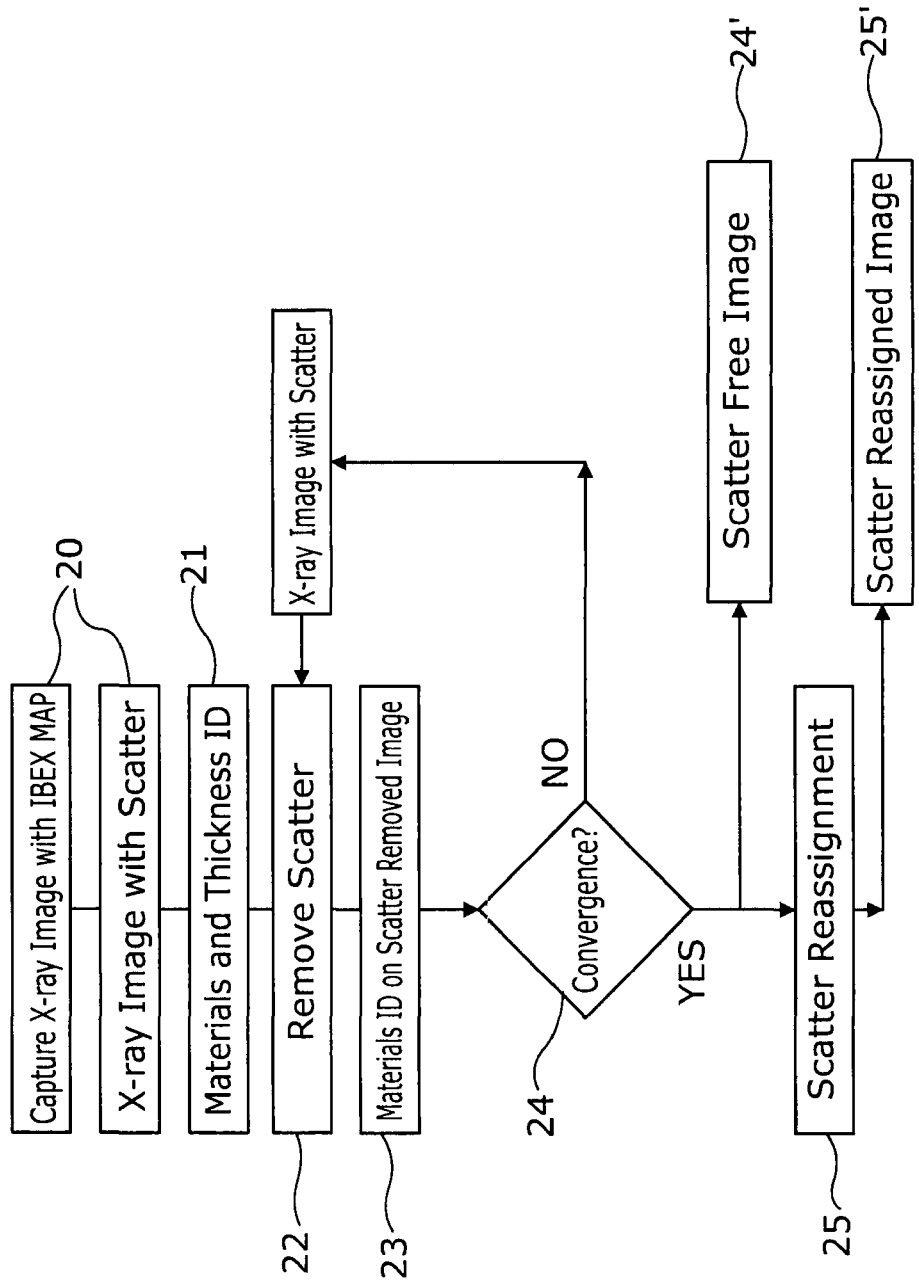
FIG. 9 is a flow chart illustrating the method of operation of the embodiment of the invention illustrated in FIGS. 8a and 8b.

FIG. 9 is a flow chart that shows how the process of the invention removes scattered x-ray photons from data recorded by the x-ray detector 2 and re-assigns the scatter photons as pseudo direct radiation.

The flow chart illustrated in FIG. 10 illustrates the process shown in FIG. 9 in greater detail, in particular, the sub-steps of resulting in a scatter free image are illustrated.

In step 20 data in the form of energy intensities are recorded by the detector 2, for each pixel thereof.

In step 21 a materials type and materials thickness identification sub-process is carried out using, for example, the technique described in UK patent application GB2498615, where the output intensities of the pixellated detector are compared with a database 30 of values that correlates the said output intensities with material identities and thicknesses. Hence, the output of this step is a material and thickness from the materials identification database 30 that is associated with each pixel of the detector 2. The term "material" includes combinations of materials. For example the output of this step may be that the material identified at a certain pixel of the detector 2 is muscle and bone. In fact, the output of this step 21 is a first estimate of the material identity and/or thickness.

In step 22 scatter kernels for the identified materials are emulated in step 22a, that is from the database of scatter kernels 31, a scatter kernel is emulated (derived) for material identified in step 21 for each pixel of the detector 2. The individual scatter kernels are convolved together in step 22b. This convolution of the scatter kernels forms what is known as the scatter estimate for the image, which is illustrated in Graph 2 in FIG. 10. As can be seen from Graph 2, there is a scatter value associated with each pixel of the detector in the scatter estimate. In step 22c the scatter in the detected x-ray intensities that represent the image is removed by subtracting the scatter intensity values from the detector output values for each pixel of the detector. The output of step 22c is shown as a scatter free image 22d, which may be an image or may be intensity values from which may be represented as an image.

It is possible that the improvement in the x-ray image could stop at this point in the process. However, it is unlikely that the first estimate of materials identity and thickness is correct, and therefore it is preferable to improve the image by more than only removing scatter radiation from the image based on a first estimate of materials identification and/or thickness.

In step 22 an initial calibration is performed so as to calibrate the detector output to the database of materials and material thicknesses.

In step 23 a materials identification step is performed on the output intensities for each pixel of the detector resulting from step 22 (these output intensities form the image). In this materials identification step, the output intensities of each pixel of the detector from step 22 are compared with a database of detector output intensities established for previously identified materials and/or thicknesses.

In step 24 a determination is made as to whether the identification of materials and/or thickness in step 23 is optimised. This is done first by comparing values representative of materials and/or thickness (or a parameter that is correlated therewith) in step 23 with the values representative of materials and/or thickness identification in step 21, and establishing whether the result of step 23 is within a threshold of the values in step 21. If the answer is NO, which it is likely to be, steps 22 and 23 are iterated until the values representative of materials and/or thickness in the current iteration of steps 22 and 23 have converged with, that is they are within a threshold of the values representative of materials and/or thickness in the previous iteration or an average of a number of previous iterations. If the answer is YES, the process moves on to step 25 where scatter is either re-assigned to produce an image with re-assigned scatter, or it is not re-assigned and a scatter free image is produced.

For each iteration, the scatter removal step 22 is performed on the X-ray image with scatter from step 20, but on each iteration the materials and/or thickness identification is from step 23 of the previous iteration, for all iterations after the first. By utilising the materials and/or thickness identification from step 23, after the scatter removal step, in the subsequent scatter removal step 22, the output of step 23 will improve, typically for a number of iterations, with the improvement per iteration diminishing with an increasing number of iterations. The materials identification in the second and subsequent iterations may be carried out in the first database used for materials and/or thickness identification in step 21 or a further database of values representative of material type and/or thickness. Such a further database or the first database itself may be populated using data collected substantially in the absence of scatter. The MAP is only required for the first estimate of materials identity and/or thickness in step 21.

Values representative of materials identification and/or thickness may include contrast, scatter kernels, scatter estimates.

With a reduced scatter effect, the materials identification in step 23 can produce a more accurate result, represented by a post convergence scatter free image 24'.

Steps 21 to 24 are reiterated until the identification of material type and thickness converges. Of course, this comparison could be with an average of a previous number of material values. The principle of operation is, however, clear. The steps 21 to 24 are reiterated until there is no substantial change in the identified material type and thickness (or a parameter that is correlated therewith).

When there is no substantial change in the materials and/or thicknesses identified, the process moves on to step 25, where the output is an image with the scatter re-assigned by adding the removed scatter radiation to the output signal at a spatial location of the detector that the x-ray photons of the removed scatter radiation would have interacted with had they not been scattered. The result of the re-assignment step 25 is represented by a re-assigned image in step 25'.

Figure 10A:
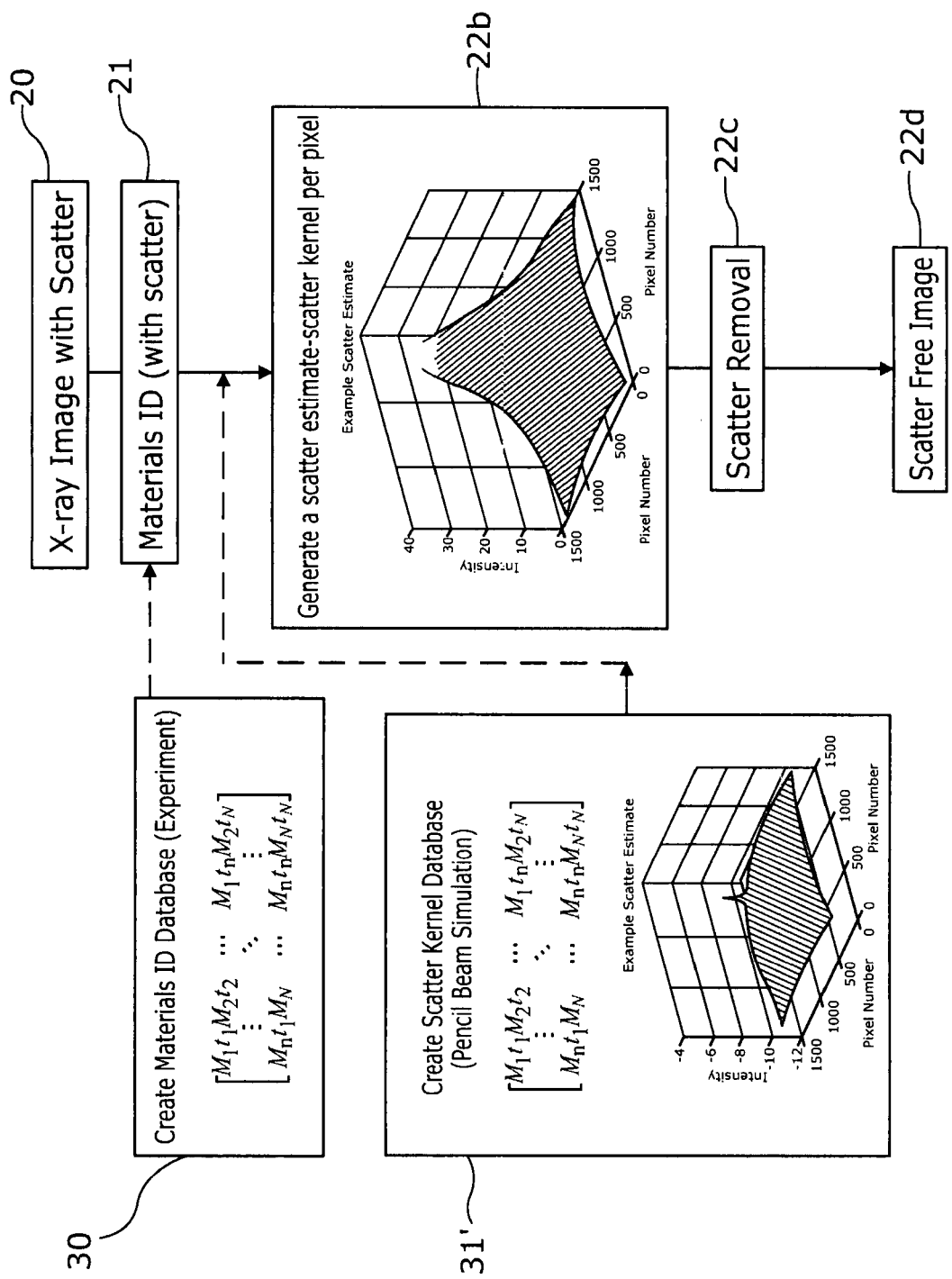
FIG. 10a is a flow chart representing an alternative method of operation of the embodiment of the invention illustrated in FIGS. 8a and 8b.

FIG. 10a illustrates an alternative process, which uses fewer steps but requires greater processing power and a larger scatter kernel database 31'. Instead of creating and using a scatter kernel database for some materials and/or thicknesses, the scatter kernel database 31' is populated with such a large number of materials and/or thicknesses that one can consider the database 31' to contain scatter kernels for all materials and/or thicknesses of interest. Hence, the interpolation step 22a, which is by emulation in the present embodiment is not required and the scatter estimate is created in step 22b directly from the scatter kernel values in the database 31'. Steps 22c and 22d are as described with reference to FIG. 10, with the output of the process being the scatter free image from step 22d.

However, whilst requiring fewer steps, the data sampling, data storage and processing power required mean that at present the process illustrated in FIGS. 9 and 10 is preferred.

FIGS. 11a to 12b illustrate the effect of performing the process of the invention illustrated in FIGS. 8a to 10.

In a simulated experiment using Monte Carlo X-ray simulation in GEANT4, a simulated sample of overlapping pieces of aluminium and plastic (PMMA), that would produce considerable scatter radiation, was used to illustrate the effectiveness of the technique. The simulation used three samples which define three regions in the image—R1, R2 and R3. R1 was a material known as PMMA and the sample was 18.5 mm thick. R2 used 18.5 mm of PMMA and 12.7 mm of aluminium. R3 used 18.5 mm of PMMA and 6.35 mm of aluminium.

The resulting image prior to scatter removal shows low contrast between adjacent regions with a contrast to noise (CNR) ratio of 16.1 between R1 and R2.

Figure 11A:
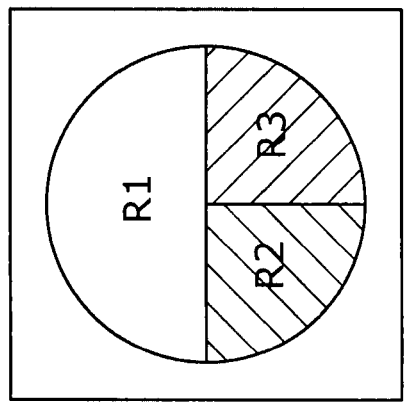
FIG. 11a shows an image of a sample detected prior to processing according to the embodiment of the invention illustrated in FIGS. 8a to 10.
Figure 11B:
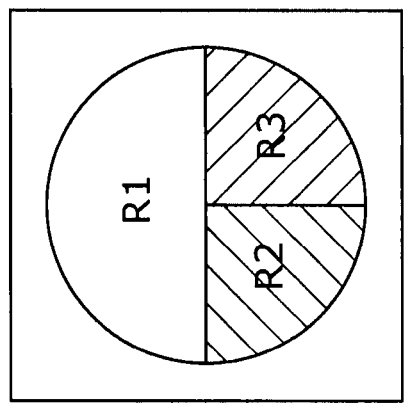
FIG. 11b shows an image of a sample detected post processing according to the embodiment of the invention illustrated in FIGS. 8a to 10.

The process illustrated in FIGS. 9 and 10 was used to reassign scatter radiation to the pixel location the x-ray photons would have interacted with had they not been scattered, and then to create a corrected image. The visual improvement in contrast between the image shown in FIG. 11a and the image shown in FIG. 11b is clear, particularly between R1 and R2. The signal to noise was 58.7 (almost 4 times better than for the uncorrected image). The histogram of FIG. 12b also illustrates the improvement. The peaks relating to R1, R2 and R3 are now well spaced apart.

Figure 12C:
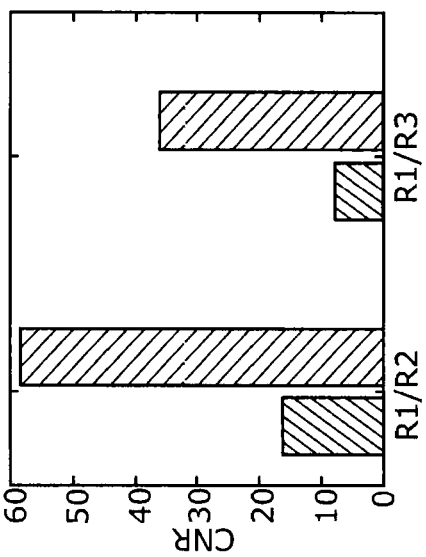
FIG. 12c is a graph showing the contrast to noise ratio for a number of regions of interest before and after scatter reassignment.
Figure 12A:
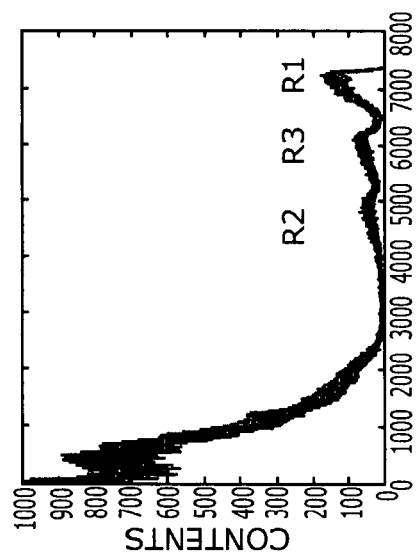
Figure 12B:
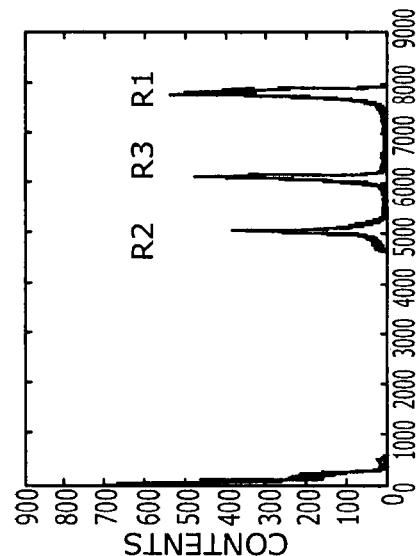
FIG. 12b shows a histogram of counts v intensity for the image shown in FIG. 11b.

FIG. 12c also demonstrates the improvement in contrast to noise ratio resulting from processing x-ray signals in accordance with the invention. The graph shows the contrast to noise ratio between R1 and R2 and R1 and R3. This is a standard measure and is calculated by taking the difference between the standard deviation of the two regions divided by the standard deviation of one region.

The invention allows scatter radiation to be better identified and therefore to be removed from the image that includes direct radiation and scatter radiation more easily.

Further, the invention allows the contrast to noise ratio to be improved either by removing scatter radiation, or by removing scatter radiation and adding it back to the output signal at a spatial location of the detector that the x-ray photons of the removed scatter radiation would have interacted with had they not been scattered.

By improving the contrast to noise ratio, either the x-ray dose may be reduced or the contrast to noise ratio increased without increasing the x-ray dose to the sample or patient. In the medical context, it is well understood that reducing dose reduces the potential for harm to patients and as such is very desirable.

The apparatus and method of the invention therefore allow x-ray dosages used in medical imaging to be reduced.

Features of the different embodiments are not exclusive to the embodiment in connection with which they are described, and may be used with other embodiments described herein.

The invention claimed is:

1. An x-ray apparatus comprising an x-ray source and a pixellated x-ray detector, the apparatus further comprising:
   a first database of values representative of material types and material thicknesses,
   a second database of scatter radiation values associated with material types and material thicknesses, and
   a processor configured to perform an algorithm which:
   i) compares an output signal of the x-ray detector with values in the first database and outputs a most likely material type and thickness from the first database;
   ii) derives from the second database scatter radiation values associated with one of the material type and material thickness as output in step (i), and the material type and material thickness as identified in a previous iteration of the algorithm;
   iii) subtracts the derived scatter radiation values from the output signal of the x-ray detector to produce a modified output signal;

iv) performs a material and thickness identification step on the modified output signal by comparing the modified signal with values in the first database; and v) utilizes the identified material and thickness in at least one further iteration of steps (ii), (iii), and (iv) of the algorithm;

wherein iteration is halted when it is determined that the modified output signal is optimized, wherein determining whether the modified output signal is optimized comprises:

comparing values indicative of material type and thickness identified in the current iteration with comparison values comprising one of:

values indicative of material type and thickness identified in a previous iteration, and averages of values indicative of material type and thickness identified in a number of previous iterations, and determining whether the values indicative of material type and thickness identified in the current iteration are within a threshold limit of the comparison values;

wherein, if the compared values are within the threshold limit, then iteration of steps (ii) to (iv) of the algorithm is halted.

2. An x-ray apparatus according to claim 1, wherein the derived scatter radiation values represent a contribution to the output signal due to scatter radiation, the contribution being removed by the subtracting step, and wherein the algorithm includes the further step of modifying the output signal of the x-ray detector by adding the removed contribution to the output signal at one or more spatial locations of the detector that x-ray photons of the scatter radiation would have interacted with had they not been scattered.

3. An x-ray apparatus according to claim 1, wherein the output signal is an x-ray output signal for each pixel of the x-ray detector.

4. An x-ray apparatus according to claim 3, wherein the algorithm is performed for the x-ray output signal for each pixel.

5. An x-ray apparatus according to claim 1, wherein the scatter radiation values in the second database of scatter radiation values associated with material types and material thicknesses are scatter kernels.

6. An x-ray apparatus according to claim 5, wherein the second database is populated with scatter kernels representing material type and thickness of some of a range of materials of interest.

7. An x-ray apparatus according to claim 6, wherein the step of subtracting the derived scatter radiation values from the output signal of the x-ray detector includes, for each pixel of the detector, the step of interpolating a scatter kernel from scatter kernels derived from the database in step (ii).

8. An x-ray apparatus according to claim 7, including the further step of generating a scatter estimate for the whole x-ray detector output signal from the interpolated scatter kernels associated with each pixel.

9. A method for improving the contrast to noise ratio in an x-ray image comprising the steps of:

i) comparing an output signal of an x-ray detector with values in a first database of values representative of material type and material thickness and outputting a most likely material type and material thickness from the first database;

ii) deriving from a second database of scatter radiation values associated with material types and material thicknesses scatter radiation values associated with one of: the material type and material thickness as output in step (i); and the material type and material thickness as identified in a previous iteration of the method;

iii) subtracting the derived scatter radiation values from the output signal of the x-ray detector to produce a modified output signal;

iv) performing a material and thickness identification step on the modified output signal by comparing the modified output signal with values in the first database; and v) utilizing the identified material and thickness in at least one further iteration of steps (ii), (iii), and (iv) of the method, wherein iteration is halted when it is determined that the modified output signal is optimized, and wherein determining whether the modified output signal is optimized comprises:

comparing values indicative of material type and thickness identified in the current iteration with comparison values comprising one of:

values indicative of material type and thickness identified in a previous iteration, and averages of values indicative of material type and thickness identified in a number of previous iterations, and determining whether the values indicative of material type and thickness identified in the current iteration are within a threshold limit of the comparison values;

wherein, if the compared values are within the threshold limit, then iteration of steps (ii) to (iv) of the method is halted.

10. The method of claim 9, wherein the derived scatter radiation values represent a contribution to the output signal due to scatter radiation, the contribution being removed by the subtracting step, the method comprising the further step of modifying the output signal of the x-ray detector by adding the removed contribution to the output signal at one or more spatial locations of the detector that x-ray photons of the scatter radiation would have interacted with had they not been scattered.

11. The method of claim 9, wherein the x-ray detector output signal is an output signal from a pixel of the x-ray detector and the method steps of claim 9 are performed on the output signal of each pixel.

12. The method of claim 9, wherein the scatter radiation values in the second database of scatter radiation values associated with material types and thicknesses are scatter kernels.

13. The method of claim 12, wherein the second database is populated with scatter kernels representing material type and thickness of some of a range of materials of interest.

14. The method of claim 13, wherein the step of subtracting the derived scatter radiation values from the output signal of the x-ray detector includes, for each pixel of the detector, the step of interpolating a scatter kernel from scatter kernels derived from the database in step (ii).

15. The method of claim 14, including the further step of generating a scatter estimate for the whole x-ray detector output signal from the interpolated scatter kernels associated with each pixel.

\* \* \* \* \*